(12) United States Patent
Jackson

(10) Patent No.: US 7,416,556 B2  
(45) Date of Patent: Aug. 26, 2008

(54) STOP-COCK SUTURE CLAMPING SYSTEM

(75) Inventor: Jasper Jackson, Newark, CA (US)

(73) Assignee: Abbott Laboratories, Abbott Park, IL (US)

( * ) Notice: Subject to any disclaimer, the term of this patent is extended or adjusted under 35 U.S.C. 154(b) by 509 days.

(21) Appl. No.: 10/162,630

(22) Filed: Jun. 6, 2002

(65) Prior Publication Data

US 2003/0229361 A1 Dec. 11, 2003

(51) Int. Cl.  
*A61B 17/04* (2006.01)
(52) U.S. Cl. .................................. 606/232
(58) Field of Classification Search ........... 24/132 AA, 24/132 R, 134 KA, 134 R; 411/34, 458, 411/907; 606/72, 74, 103, 139, 142, 144, 606/147, 148, 151, 232, 1
See application file for complete search history.

(56) References Cited

U.S. PATENT DOCUMENTS

| | | | | |
|---|---|---|---|---|
| 1,088,892 | A * | 3/1914 | Foreman | 411/418 |
| 1,811,738 | A * | 6/1931 | Williams | 84/297 R |
| 1,852,098 | A | 4/1932 | Anderson | |
| 2,075,508 | A | 3/1937 | Davidson | |
| 2,104,192 | A * | 1/1938 | Ford | 433/10 |
| 2,557,877 | A * | 6/1951 | Kluson | 84/304 |
| 2,751,802 | A * | 6/1956 | Reuillard | 81/124.3 |
| 2,896,448 | A * | 7/1959 | Haines | 73/858 |
| 3,014,483 | A | 12/1961 | McCarthy | |
| 3,306,291 | A * | 2/1967 | Burke | 604/110 |
| 3,513,848 | A | 5/1970 | Winston | |
| 3,525,340 | A | 8/1970 | Gilbert | |
| 3,589,369 | A * | 6/1971 | Alksnis | 606/210 |
| 3,664,345 | A | 5/1972 | Dabbs et al. | |
| 3,732,719 | A | 5/1973 | Pallotta | |
| 3,750,650 | A | 8/1973 | Ruttgers | |
| 3,753,438 | A | 8/1973 | Wood et al. | |
| 3,829,903 | A * | 8/1974 | Stati et al. | 600/36 |
| 3,831,608 | A | 8/1974 | Kletschka et al. | |

(Continued)

FOREIGN PATENT DOCUMENTS

SU 197801 1/1978

(Continued)

OTHER PUBLICATIONS

McCarthy, et al., "Tension (Stay) Suture Bridge", *J. of International College of Surgeons*, 34(5), pp. 613-614 (Nov. 1960).

*Primary Examiner*—Todd Manahan  
*Assistant Examiner*—Tuan V. Nguyen  
(74) *Attorney, Agent, or Firm*—Workman Nydegger (57) ABSTRACT

A suture clamping system, comprising a block of material having a hole passing therethrough; and a rotatable element received into the block of material, the rotatable element having a hole passing therethrough, wherein the rotatable element can be positioned such that the hole passing through the block of material and the hole passing through the rotatable element can be placed in alignment forming a passageway through both the block of material and the rotatable element. A method of clamping a suture, comprising passing the suture through a passageway which extends both through a block of material and through a hole in a rotatable element received into the block of material; and turning the rotatable element, and winding the suture pair around the rotatable element within the block of material.

12 Claims, 11 Drawing Sheets

U.S. PATENT DOCUMENTS

| | | | |
|---|---|---|---|
| 3,845,772 A * | 11/1974 | Smith | 606/232 |
| 3,931,821 A | 1/1976 | Kletschka et al. | |
| 3,976,079 A | 8/1976 | Samuels et al. | |
| 4,287,489 A | 9/1981 | Pinkham | |
| 4,291,698 A | 9/1981 | Fuchs et al. | |
| 4,387,489 A | 6/1983 | Dudek | |
| 4,505,274 A | 3/1985 | Speelman | |
| 4,506,568 A * | 3/1985 | Aamodt | 81/64 |
| 4,577,635 A | 3/1986 | Meredith | |
| 4,644,956 A | 2/1987 | Morgenstern | |
| 4,667,675 A | 5/1987 | Davis | |
| 4,683,895 A | 8/1987 | Pohndorf | |
| 4,750,492 A * | 6/1988 | Jacobs | 606/230 |
| 4,773,421 A | 9/1988 | Davis | |
| 4,813,586 A | 3/1989 | Seifert | |
| 4,823,794 A | 4/1989 | Pierce | |
| 4,866,818 A | 9/1989 | Thompson | |
| 5,009,663 A | 4/1991 | Broome | |
| 5,071,430 A | 12/1991 | de Salis et al. | |
| 5,078,731 A | 1/1992 | Hayhurst | |
| 5,158,566 A | 10/1992 | Pianetti | |
| 5,160,339 A | 11/1992 | Chen et al. | |
| 5,171,251 A | 12/1992 | Bregen et al. | |
| 5,176,682 A | 1/1993 | Chow | |
| 5,203,787 A | 4/1993 | Noblitt et al. | |
| 5,219,359 A | 6/1993 | McQuilkin et al. | |
| 5,234,449 A | 8/1993 | Bruker et al. | |
| 5,236,445 A | 8/1993 | Hayhurst et al. | |
| 5,258,015 A | 11/1993 | Li et al. | |
| 5,282,832 A | 2/1994 | Toso et al. | |
| 5,306,280 A | 4/1994 | Bregen et al. | |
| 5,330,442 A | 7/1994 | Green et al. | |
| 5,354,292 A * | 10/1994 | Braeuer et al. | 606/1 |
| 5,376,101 A | 12/1994 | Green et al. | |
| 5,383,905 A | 1/1995 | Golds et al. | |
| 5,391,173 A | 2/1995 | Wilk | |
| 5,409,499 A | 4/1995 | Yi et al. | |
| 5,462,558 A | 10/1995 | Kolesa et al. | |
| 5,474,572 A | 12/1995 | Hayhurst | |
| 5,501,698 A | 3/1996 | Roth et al. | |
| 5,514,159 A | 5/1996 | Guillotine | |
| 5,521,184 A | 5/1996 | Zimmermann | |
| 5,534,011 A * | 7/1996 | Greene et al. | 606/232 |
| 5,543,520 A | 8/1996 | Zimmermann | |
| 5,584,835 A * | 12/1996 | Greenfield | 606/232 |
| 5,593,422 A | 1/1997 | Mujis van de Moer | |
| 5,593,425 A | 1/1997 | Bonutti et al. | |
| 5,611,986 A | 3/1997 | Datta et al. | |
| 5,618,306 A | 4/1997 | Roth et al. | |
| 5,630,824 A | 5/1997 | Hart | |
| 5,645,553 A | 7/1997 | Kolesa et al. | |
| 5,669,917 A | 9/1997 | Sauer et al. | |
| 5,681,351 A | 10/1997 | Jamiolkowski et al. | |
| 5,709,708 A | 1/1998 | Thal | |
| 5,720,765 A | 2/1998 | Thal | |
| 5,725,556 A | 3/1998 | Moser et al. | |
| 5,728,109 A | 3/1998 | Schulze et al. | |
| 5,735,875 A | 4/1998 | Bonutti et al. | |
| 5,735,877 A | 4/1998 | Pagedas | |
| 5,749,898 A | 5/1998 | Schulze et al. | |
| 5,769,862 A | 6/1998 | Kammerer et al. | |
| 5,776,150 A | 7/1998 | Nolan et al. | |
| 5,782,864 A | 7/1998 | Lizardi | |
| 5,810,877 A | 9/1998 | Roth et al. | |
| 5,814,069 A | 9/1998 | Schulze et al. | |
| 5,846,254 A | 12/1998 | Schulze et al. | |
| 5,871,490 A | 2/1999 | Schulze et al. | |
| 5,893,592 A | 4/1999 | Schulze et al. | |
| 5,919,208 A | 7/1999 | Valenti | |
| 5,976,159 A | 11/1999 | Bolduc et al. | |
| 5,984,933 A * | 11/1999 | Yoon | 606/148 |
| 6,024,758 A | 2/2000 | Thal | |
| 6,066,160 A | 5/2000 | Colvin et al. | |
| 6,074,409 A | 6/2000 | Goldfarb | |
| 6,086,608 A * | 7/2000 | Ek et al. | 606/232 |
| 6,099,553 A | 8/2000 | Hart et al. | |
| 6,106,545 A | 8/2000 | Egan | |
| 6,126,677 A | 10/2000 | Ganaja et al. | |
| 6,143,017 A | 11/2000 | Thal | |
| 6,152,934 A | 11/2000 | Harper et al. | |
| 6,159,243 A | 12/2000 | Bonutti et al. | |
| 6,165,204 A | 12/2000 | Levinson et al. | |
| 6,174,324 B1 | 1/2001 | Egan et al. | |
| 6,200,329 B1 | 3/2001 | Fung et al. | |
| 6,203,565 B1 | 3/2001 | Bonutti et al. | |
| 6,231,592 B1 | 5/2001 | Bonutti et al. | |
| 6,254,615 B1 | 7/2001 | Bolduc et al. | |
| 2003/0105462 A1 * | 6/2003 | Haider | 606/69 |

FOREIGN PATENT DOCUMENTS

| | | |
|---|---|---|
| WO | WO 95/21573 | 8/1975 |
| WO | WO 97/28745 | 8/1997 |

* cited by examiner

STOP-COCK SUTURE CLAMPING SYSTEM

TECHNICAL FIELD

The present invention relates to systems for securing a pair of suture lengths together or for using a single strand of suture to secure tissues together at an operative site in a patient without necessarily tying a knot.

BACKGROUND OF THE INVENTION

Sutures are used to sew tissue together, and thereby close tissue openings, cuts or incisions during or after any of a very wide variety of medical procedures. Typically, the surgeon manually ties together a suture pair to close the opening, however, automatic suture tying systems have also been developed.

There are a number of disadvantages of knotting sutures together to secure tissues to one another. For example, manual knot tying requires considerable dexterity. Also, manual knot tying can take considerable time. Knot tying is further complicated by the fact that surgical sutures have low friction surfaces. Therefore, it is typically necessary for a surgeon to include many "throws" when tying the knot. This multiple-throw problem occurs even if an automatic knot tying device is used. Unfortunately, as the number of loops or "throws" incorporated into the knot increase, the knot becomes increasingly large and bulky. Moreover, the surgeon typically needs to handle strands of adequate suture length prior to commencing manual knot tying. Thus, manual knot tying requires considerable space both in which to view, and to perform, the actual suture knot tying. Therefore, knot tying is particularly difficult in areas of limited available space or access, for example, at the back of the patient's heart during a coronary artery bypass graft (CABG) operation. Manually tied knots often lock prior to reaching the intended amount of tension to be applied to the tissue. Furthermore, tissues are typically secured together by a pair of sutures wherein each of the sutures in the pair pass through both of the tissues which are secured together by tying off the suture pair. It would instead be advantageous to provide a system which is adapted to secure together two tissues, but uses only a single strand of suture.

SUMMARY OF THE INVENTION

Embodiments of the present invention provide a suture clamping system. In one embodiment, the suture clamping system includes a block of material having a hole defined therethrough, and a rotatable element received into the block of material. The rotatable element has a hole defined therethrough. The rotatable element can be positioned such that the hole passing through the block of material and the hole passing through the rotatable element can be placed in alignment forming a passageway through both the block of material and the rotatable element.

In preferred aspects, the present invention can be used for clamping a suture pair together. Such suture pair may have two different suture strands or opposite ends of a single suture strand. In alternate aspects, the present invention can also be used to clamp onto a single strand of suture, for instance, where the present system operates as a suture anchor.

In preferred aspects, the system further includes a rod for turning the rotatable element, wherein the distal end of the rod is dimensioned to mate with an end of the rotatable element which projects out of the block of material.

In one preferred embodiment, the system includes an elongated positioning member dimensioned to receive both the rod and the block of material therein. Specifically, the block of material may be received into a distal end of the elongated positioning member, with the rod being positioned within a chamber or lumen passing through the elongated positioning member. As such, the rod may be moved distally such that it can push the block of material out of the distal end of the positioning member, after the suture(s) has/(have) been clamped together.

The present invention further provides an embodiment comprising a plurality of the above blocks (each block having a rotatable element received therein) being separated by thin members. Optionally, such thin members may be cut such that the individual suture pairs may be separated from one another, after the pairs have each been clamped together.

The present invention further includes a method of clamping a single suture or a suture pair, comprising passing the suture(s) through a passageway which goes both through a block of material and through a hole in a rotatable element received into the block of material; and turning the rotatable element, thereby winding the suture(s) around the rotatable element within the block of material. Turning the rotatable element may optionally include rotating a rod, wherein the distal end of the rod is dimensioned and positioned to mate with an end of the rotatable element which projects out of the block of material. Additionally, by distally advancing the rod, the block of material may optionally be easily pushed out of a distal end of the elongated positioning member.

Features of the present invention allow a physician to completely avoid manual suture knot tying. Therefore, the bulky multiple loops or "throws" required when knot tying can be minimized or eliminated. Instead, a suture pair is simply "clamped" or held together by being wrapped around the rotatable element. Alternatively, the present system can be clamped onto a single suture and can thus act as an anchor preventing movement of a tissue layer along a single suture strand. Furthermore, the block of material preferably includes an elastic material which deforms to accommodate the suture (s) as it is wrapped around the rotatable element.

Embodiments of the present system can be positioned directly adjacent to the operative site at which it is desirable to secure the suture(s) together. Specifically, by first advancing the block of material (with the suture(s) passing therethrough) to a position close to the operative site and then turning the rotatable element, the applicator portion of the system can be used to fasten together a suture pair, or position the present assembly, right at the operative site.

The present system can minimize the extent to which suture at the surgical site is pulled as it secures the suture(s). As the present system is deployed, it simply tightens together the suture(s) at the operative site. In contrast, when tying together a suture pair, it is typically difficult to tie a knot very close to the operative site without excessively pulling on the tissues being tied together.

Thus, the present invention provides a rapid, easily operated, system to secure a suture pair together, or to provide a tissue anchor along a single strand of suture.

DETAILED DESCRIPTION OF THE DRAWINGS

The present invention provides systems and methods for clamping suture(s) without necessitating the tying of a knot. In a simplified preferred aspect, as shown in FIGS. 1 to 4C, a suture clamping system 10 is provided. System 10 includes a block of material 12 having a hole 13 defined therethrough; and a rotatable element 14 (which is received into block 12) having a hole 15 defined therethrough. Rotatable element 14 can be positioned such that hole 13 and hole 15 can be placed in alignment forming a passageway through both block 12 and rotatable element 14.

Figure 1:
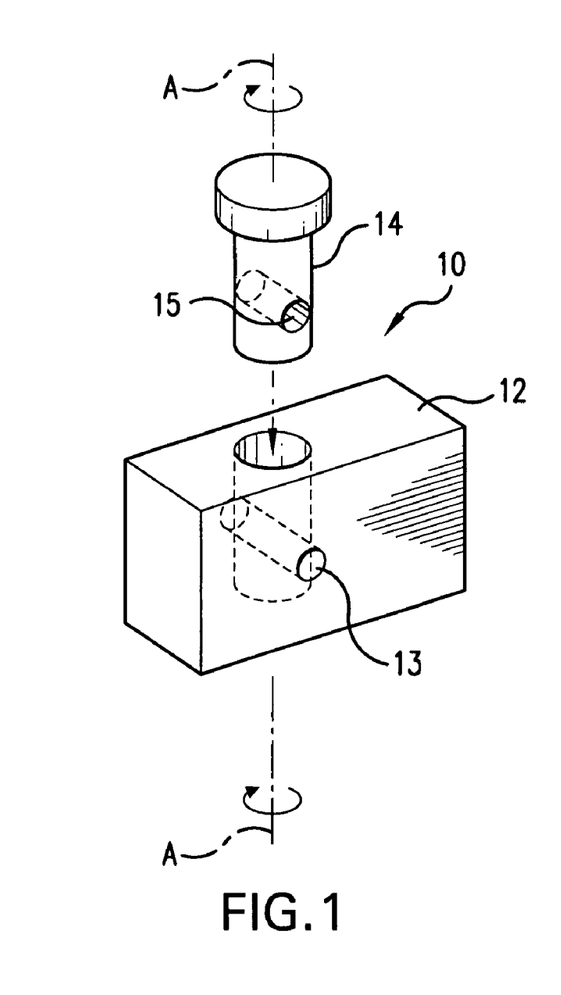
FIG. 1 is an exploded perspective view of a simplified embodiment of the present invention.
Figure 2:
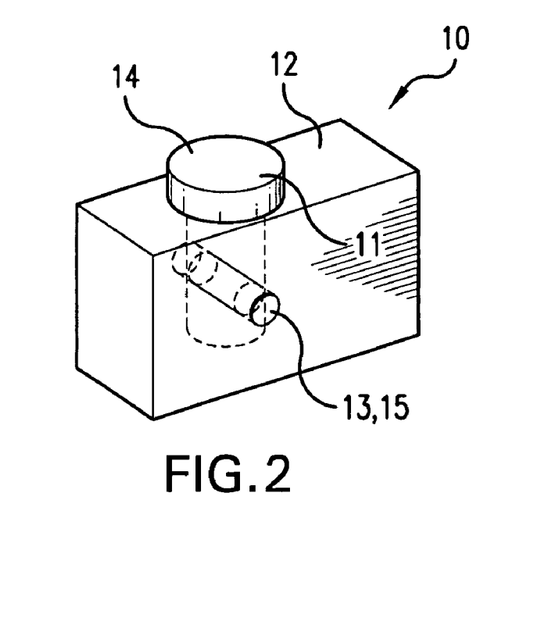
FIG. 2 is an assembled perspective view of a simplified embodiment of the system of FIG. 1.

For ease of illustration, rotatable element 14 is shown to rotate about axis A, wherein axis A is generally perpendicular to both holes 13 and 15. It is not necessary for axis A to be perpendicular to the holes. In preferred aspects, block 12 is made of an elastic material such as silicone or polypropylene, or other suitable soft, elastic material. In preferred aspects, rotatable element 14 is made of stainless steel or moldable plastic. Rotatable element 14 is made to a dimension such that it is preferably "friction-fit" or "press-fit" into block 12 such that element 14 may be rotated, but does not tend to fall out of block 12. Alternatively, a retaining mechanism, such as a flange or housing may be provided.

Figure 3A:
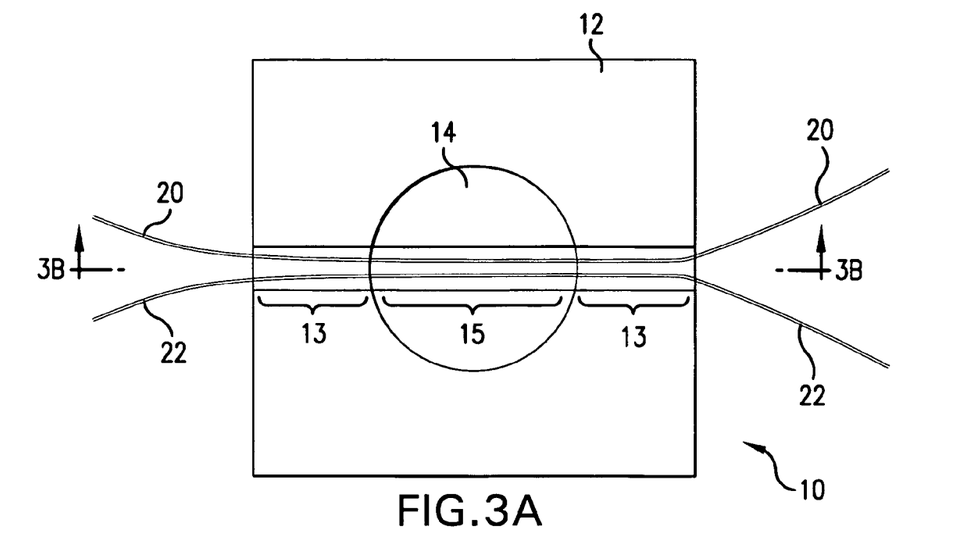
FIG. 3A is a top sectional view of the system of FIG. 1, showing a suture pair received therethrough (prior to clamping together the suture pair).
Figure 3B:
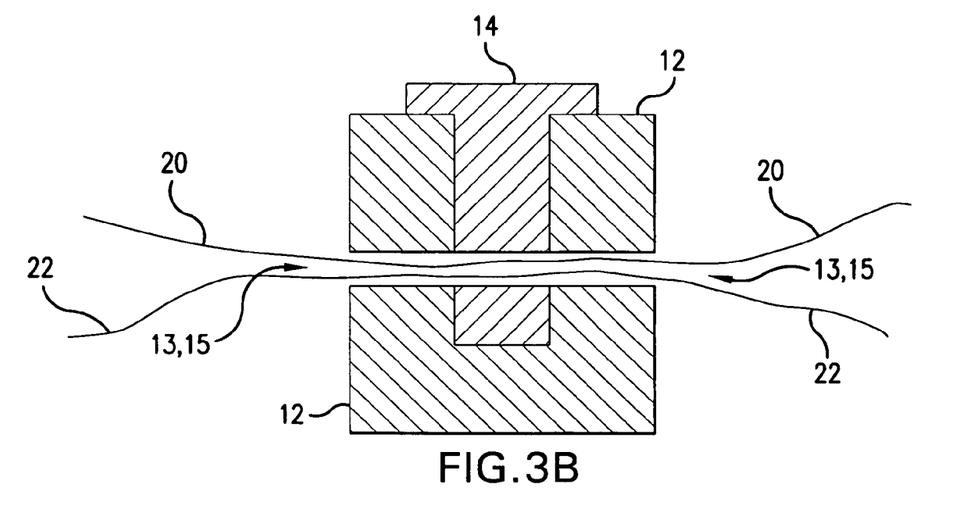
FIG. 3B is a sectional side elevation view taken along line 3B-3B in FIG. 3A.
Figure 4A:
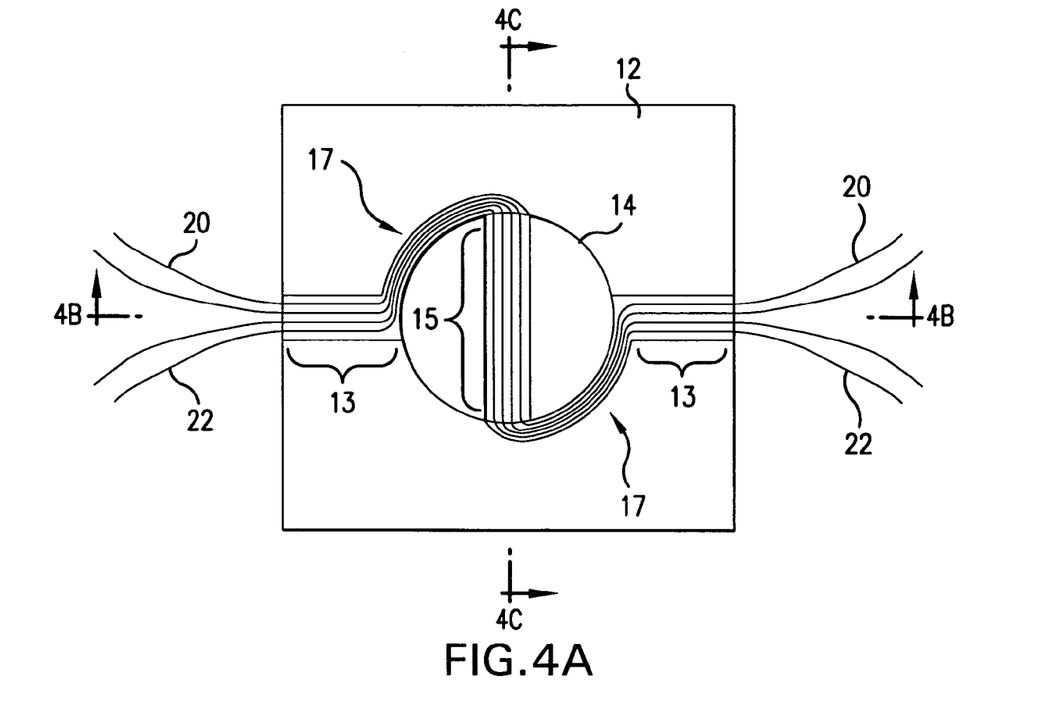
FIG. 4A is a top sectional view of the system of FIG. 1, after turning the rotatable element 90 degrees.
Figure 4B:
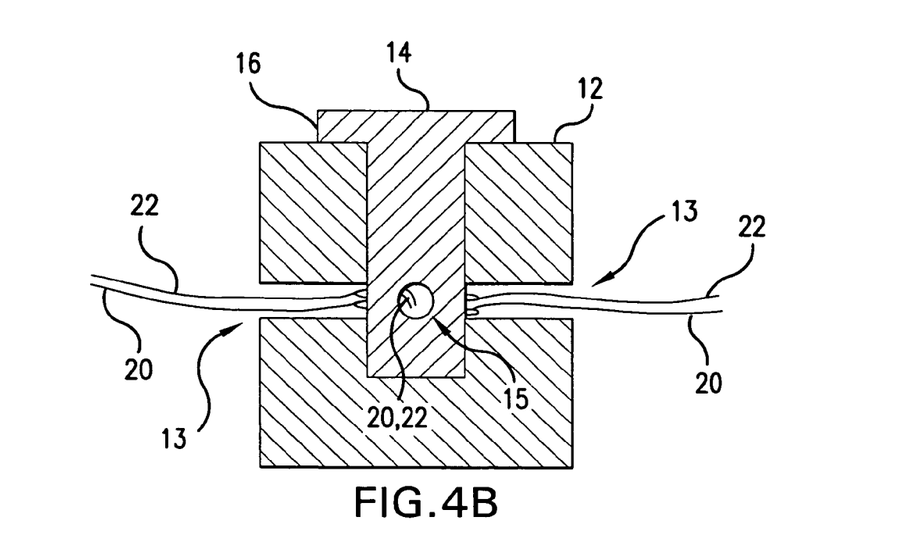
FIG. 4B is a sectional side elevation view taken along line 4B-4B in FIG. 4A.
Figure 4C:
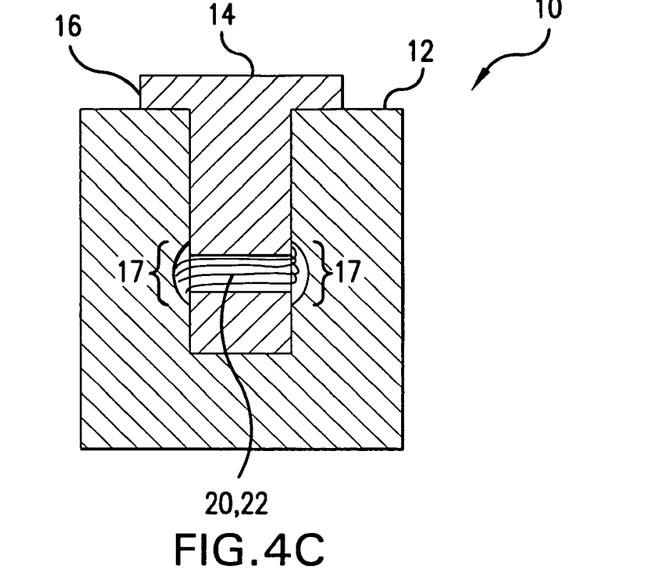
FIG. 4C is a sectional side elevation view taken along line 4C-4C in FIG. 4A.

A preferred method of operation of the invention is illustrated in FIGS. 3A to 4C, as follows. As seen in FIGS. 3A and 3B, a suture pair 20 and 22 is first fed through holes 13 and 15, thereby passing fully through system 10. Then, as shown in FIG. 4A, element 14 is rotated (here, by 90 degrees from FIG. 3A) thereby forming a tortuous path for suture pair 20 and 22. As can be appreciated, rotation of element 14 within block 12 will tightly hold suture pair 20 and 22 together. It is to be understood that, although element 14 is illustrated as being rotated by 90 degrees from FIG. 3A to FIG. 4A, greater or lesser amounts of rotation may instead be used. For example, element 14 may instead be rotated around many times such that sutures 20 and 22 are wrapped several times around element 14. Conversely, as can be seen in FIG. 4A, even a partial rotation of element 14 will result in regions 17 in which sutures 20 and 22 are compressed between element 14 and block 12. Preferably, therefore, block 12 will deform to a degree to receive suture pair 20 and 22 between the outer surface of element 14 and the inner surface of block 12. FIGS. 4B and 4C show corresponding sectional views along lines 4B-4B and 4C-4C in FIG. 4A, respectively.

In additional aspects of the invention, only a single suture strand (e.g.: 20 or 22) is used. Thus, the present system can secured to a single suture strand, and thus act as an anchor which prevents tissue movement along the single suture strand.

Figure 5:
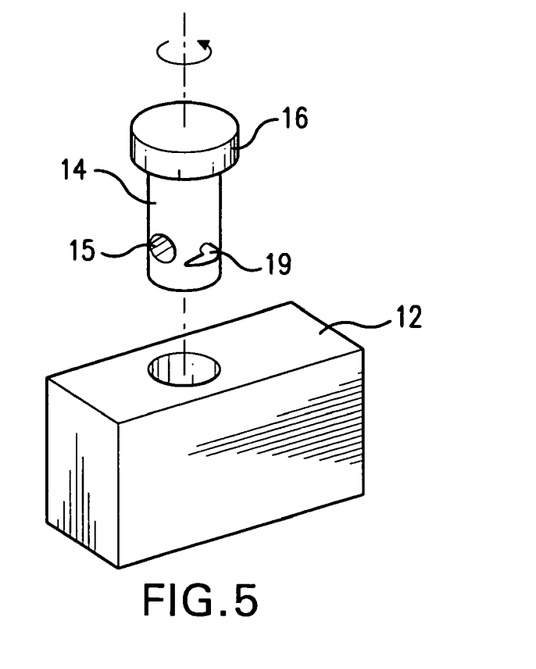
FIG. 5 is a exploded perspective view of an alternate embodiment of the invention having a curved barb extending from the rotatable element.
Figure 6:
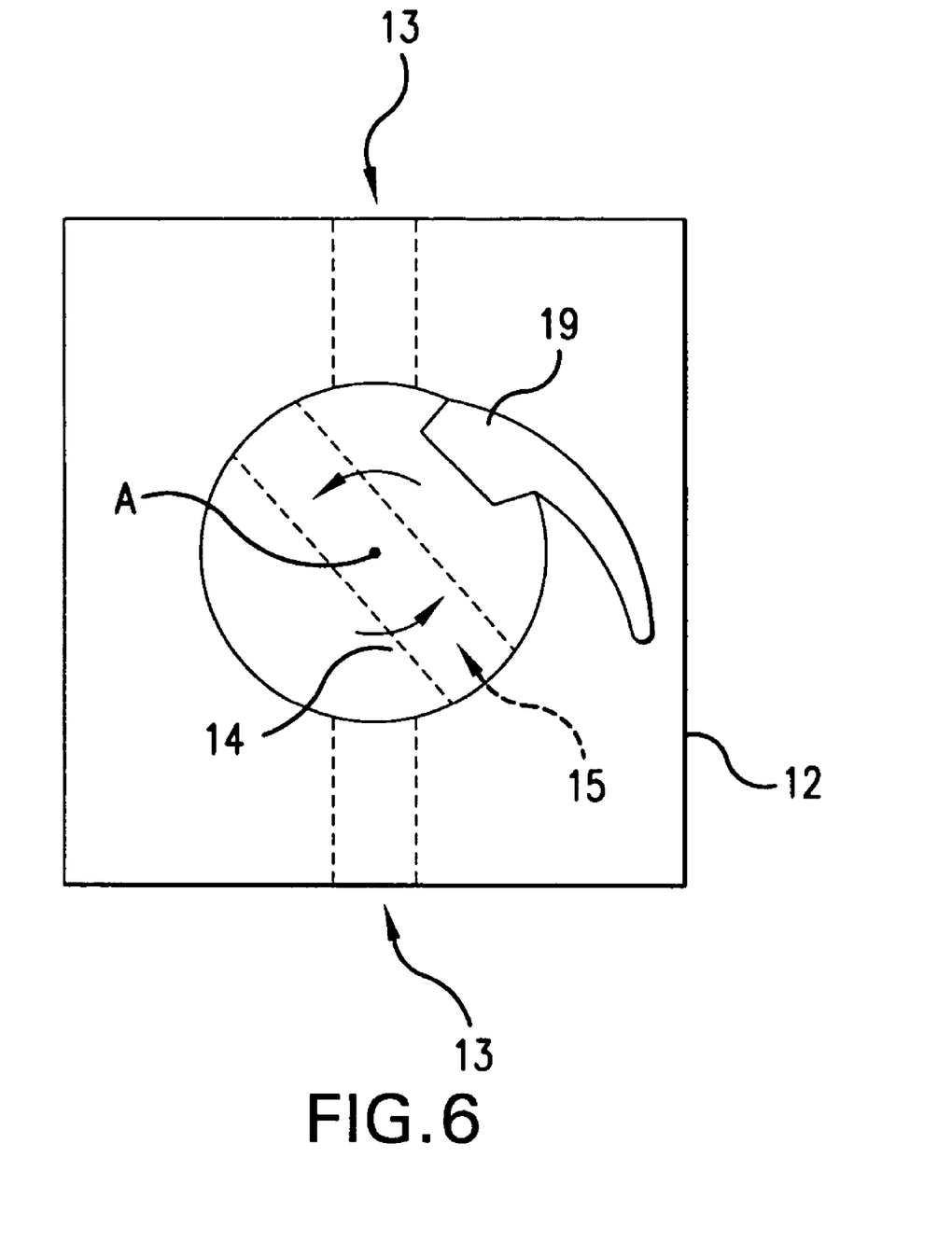
FIG. 6 is a sectional top plan view of the embodiment of FIG. 5.

In an optional aspect of the invention, as illustrated in FIGS. 5 and 6, rotatable element 14 includes a projection such as curved barb 19 which inhibits rotation of element 14 in one direction. As shown in FIG. 6, curved barb 19 is preferably disposed in a plane perpendicular to axis of rotation A of rotatable element 14.

Figure 7:
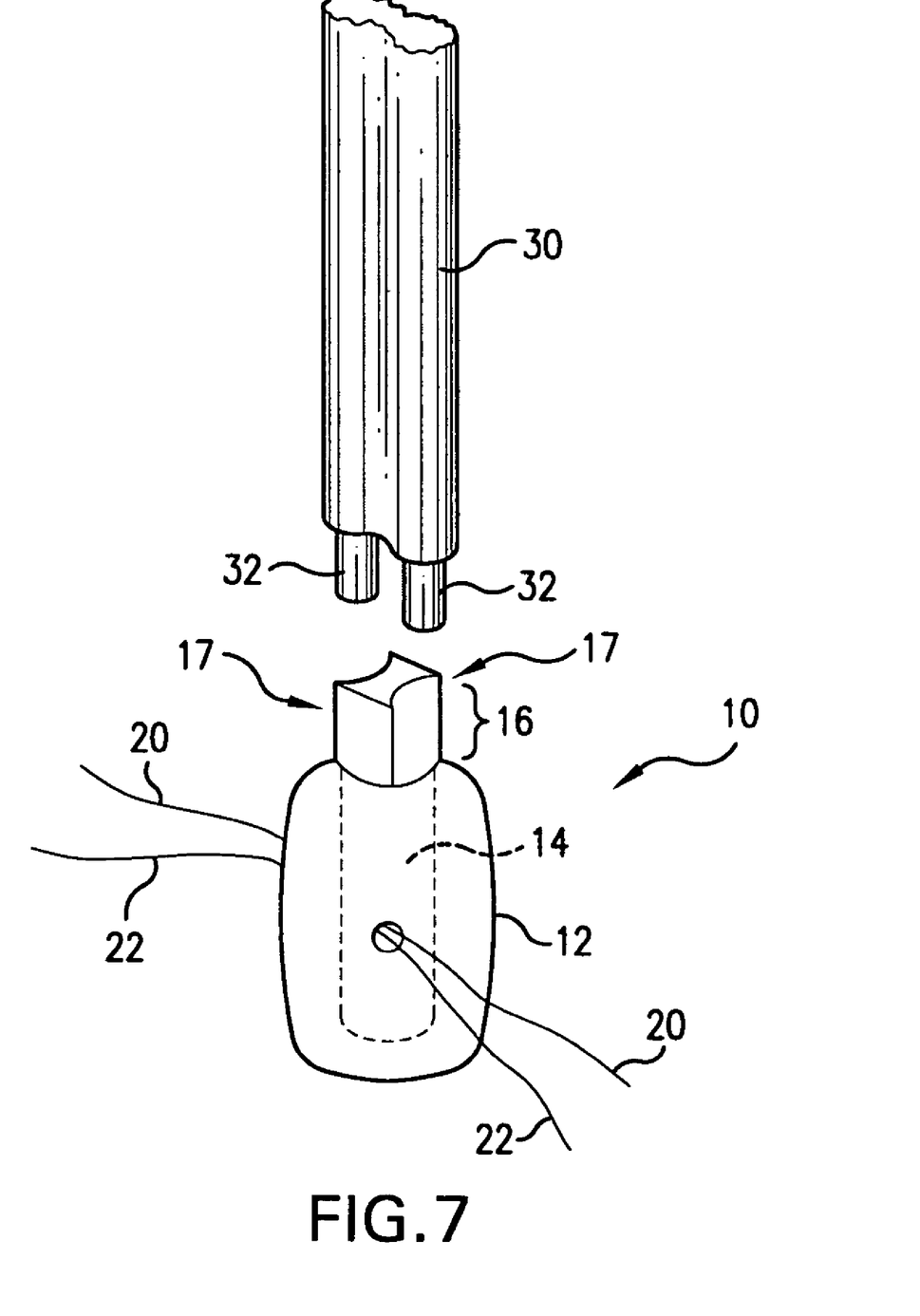
FIG. 7 is a perspective view of an alternate embodiment of the present invention, showing an instrument adapted to mate with and rotate the rotatable element, thereby clamping together a suture pair.
Figure 9A:
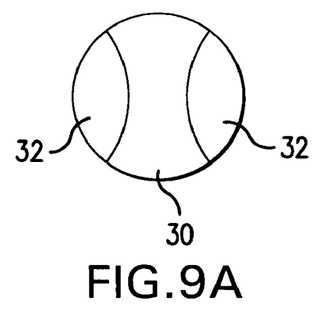
FIGS. 9A and 9B show the bottom end of the rod and the top end of the rotatable element dimensioned to mate with one another, respectively.
Figure 9B:
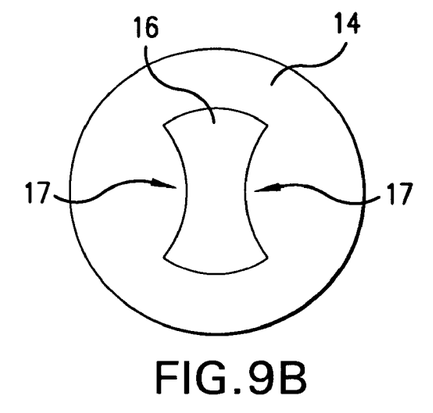
Figure 9C:
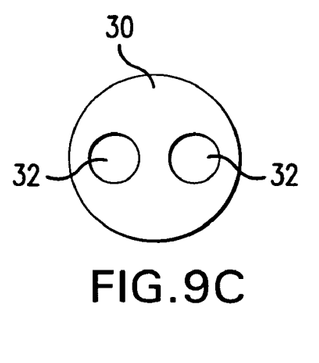
FIGS. 9C and 9D show the bottom end of the rod and the top end of the rotatable element dimensioned to mate with one another, respectively.
Figure 9D:
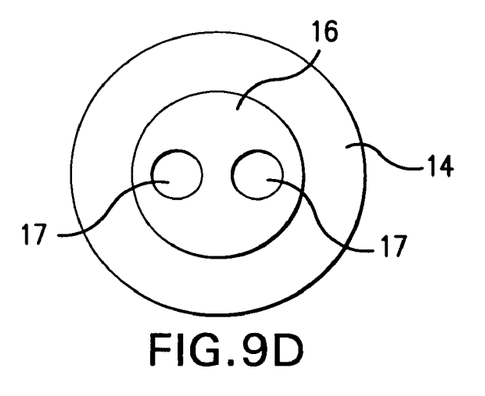

As can be seen in FIGS. 2, 4B, 4C and 5, an end 16 of rotatable element 14 may project out of block 12. Rotatable element 14 is turned by turning end 16. It is to be understood that end 16 may alternatively project out of, or be recessed into, block 12. By coupling a rotation device against end 16, element 14 can be rotated. For example, as illustrated in FIG. 7, for example, a rod 30 having a pair of projections 32 at its distal end may be used to engage recesses 17 in end 16 of element 14. Thereby, by turning rod 30, element 14 is rotated. FIGS. 9A and 9B also show this embodiment of present invention. FIGS. 9C and 9D show an alternate embodiment with projections 32 (on the distal end of rod 30) are similarly received into recesses 17 on the top of end 16 of element 14. It is to be understood that rod 30 may instead include recesses in its distal end into which projections from end 16 of element 14 are received.

Figure 8:
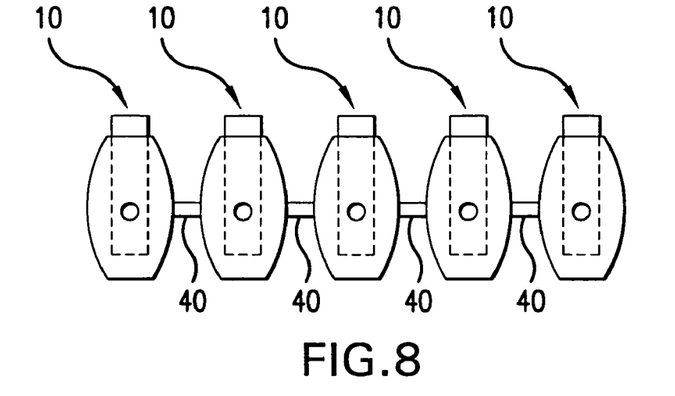
FIG. 8 is a front elevation view of a system comprising a plurality of the embodiments of FIG. 7 linked together by short thin members.

FIG. 8 shows an embodiment of the invention in which a plurality of system 10's are linked together (preferably with thin members 40 spanning therebetween). In this embodiment, members 40 can easily be cut apart or separated to prevent multiple sutures from becoming strained or fixed to an adjacent system 10. The suture(s) of a single system 10 can be tightened together or independently of one another. Separate system 10's are also advantageous if one needs to be replaced. Moreover, having a plurality of system 10's linked together also provides an operator with a larger overall "package" to manipulate. This is particularly advantageous when individual system 10's are very small.

In preferred aspects, the various blocks of material 12 and the thin members 40 spanning therebetween are formed from a single unitary block of material.

Figure 10:
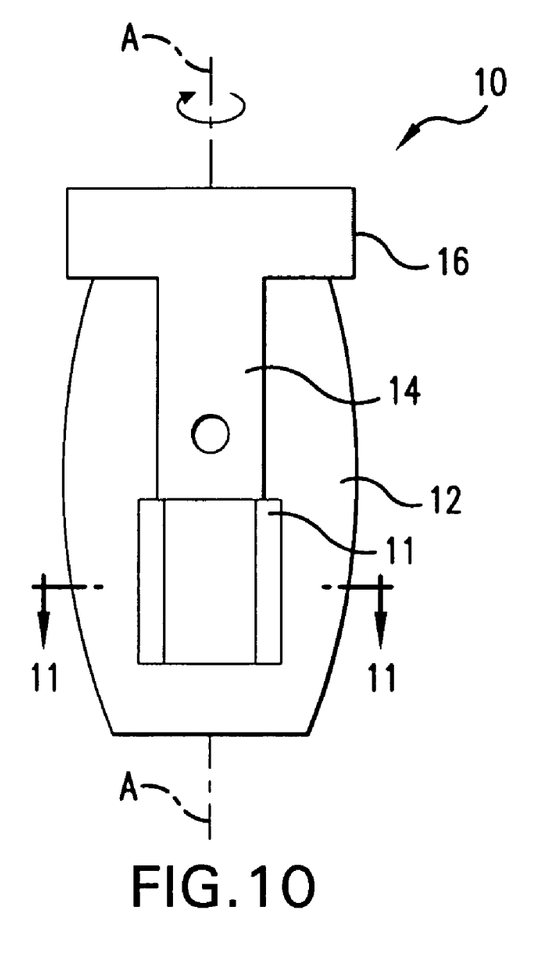
FIG. 10 is a schematic side elevation view of an alternate embodiment of the present invention.
Figure 11:
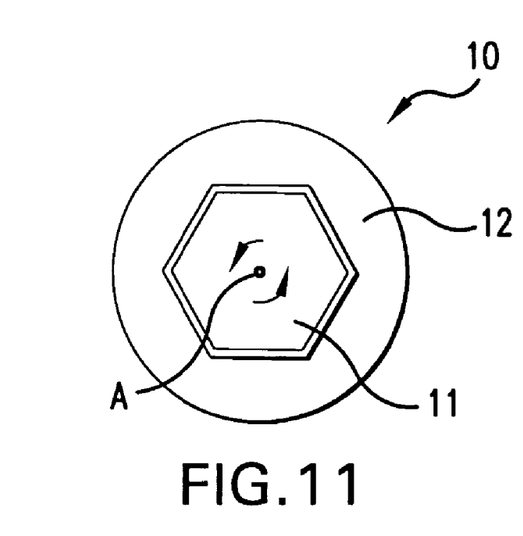
FIG. 11 is a view taken along line 11-11 in FIG. 10.

FIGS. 10 and 11 show an embodiment of the invention in which rotatable element 14 has a distal end 11 with a symmetric, non-circular cross section. As illustrated in FIG. 11, end 11 may be hexagonal, but square, octagonal or other shaped ends are also contemplated. As can be appreciated, rotating element 14 around axis A will tend to result in element 11 clicking from one position to the next. The symmetric, non-circular cross section provides resistance such that element 14 will not inadvertently rotate backwards and thus unwind.

Figure 12:
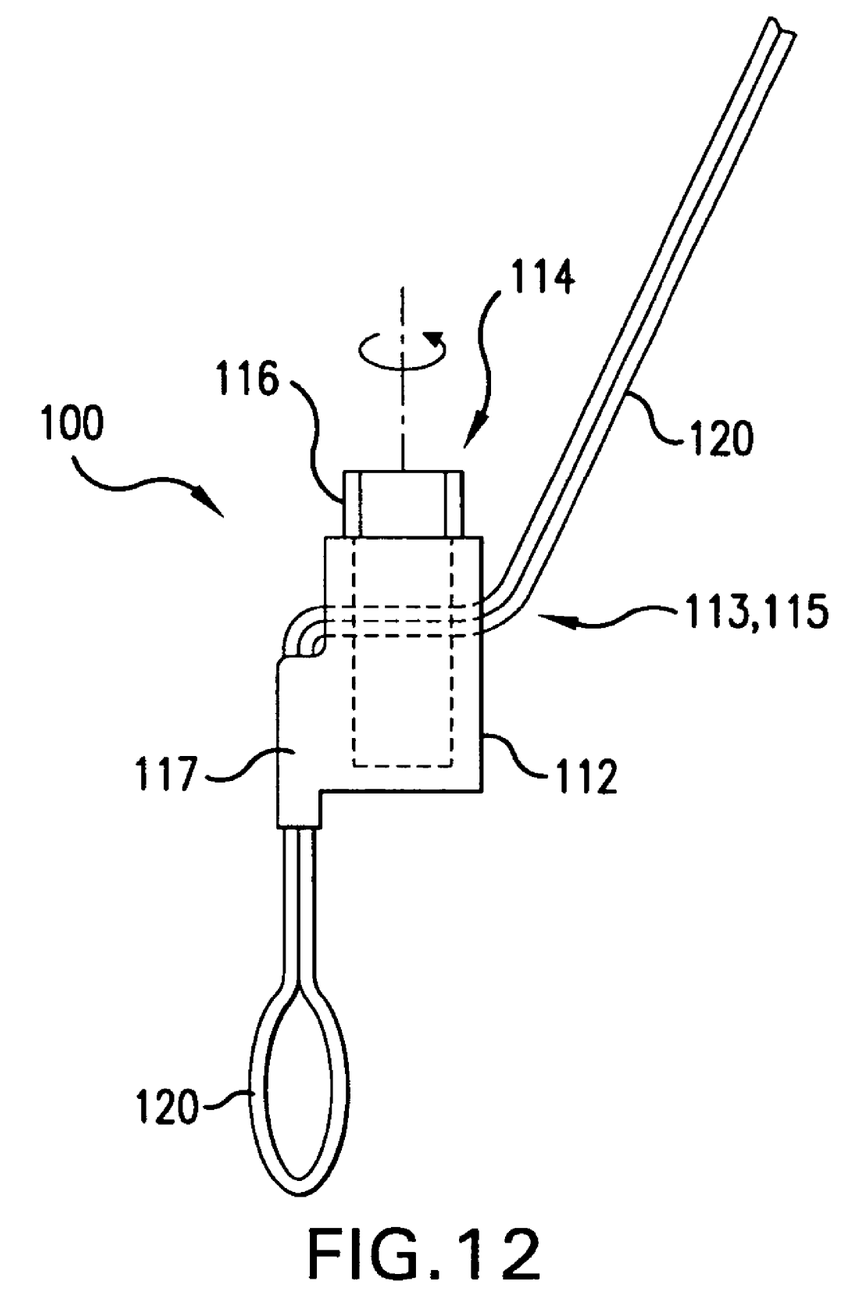
FIG. 12 is a schematic side elevation view of an alternate embodiment of the present invention.
Figure 13:
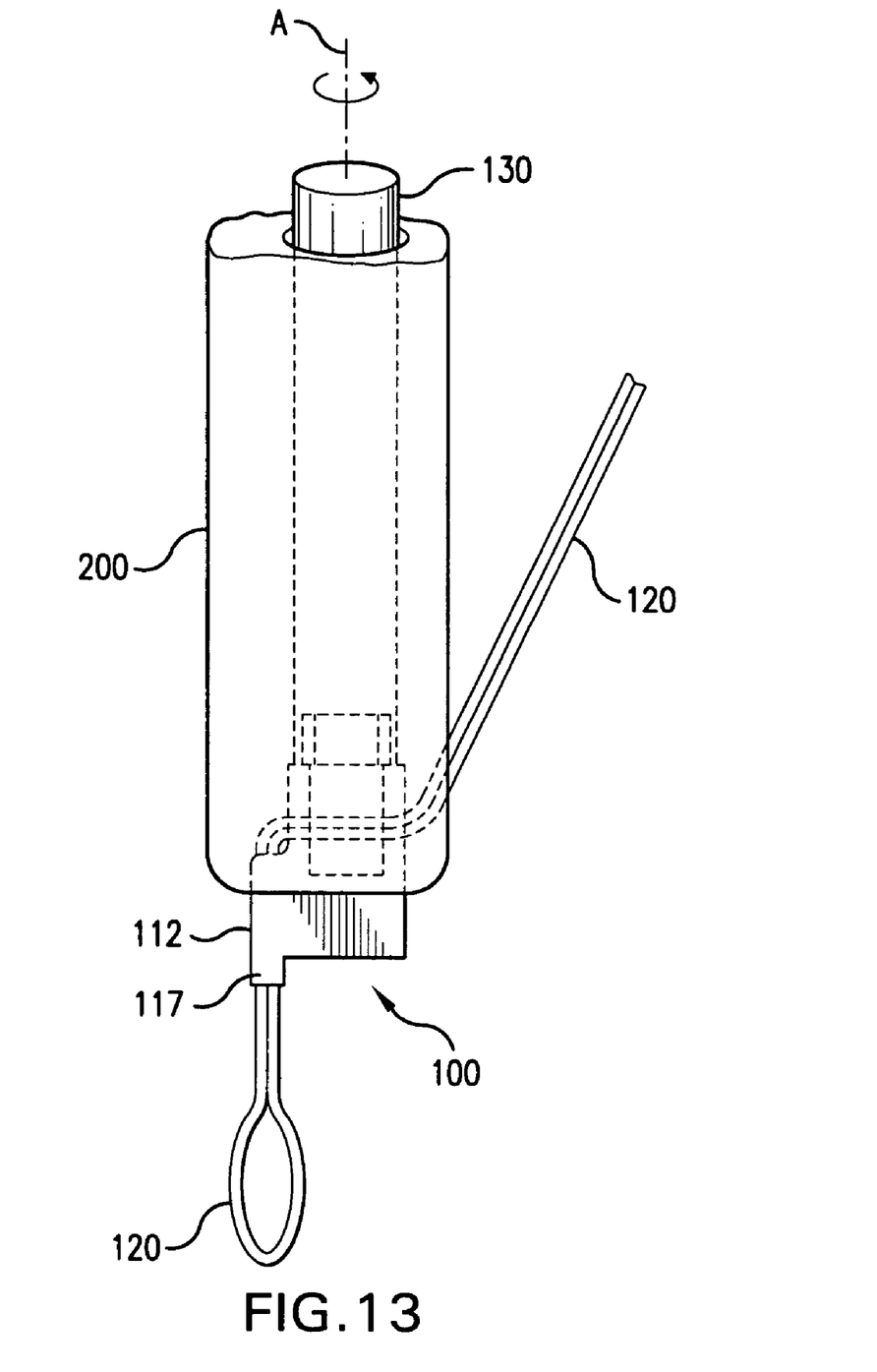
FIG. 13 is a side elevation view of a system for operating the embodiment of FIG. 12.
Figure 14:
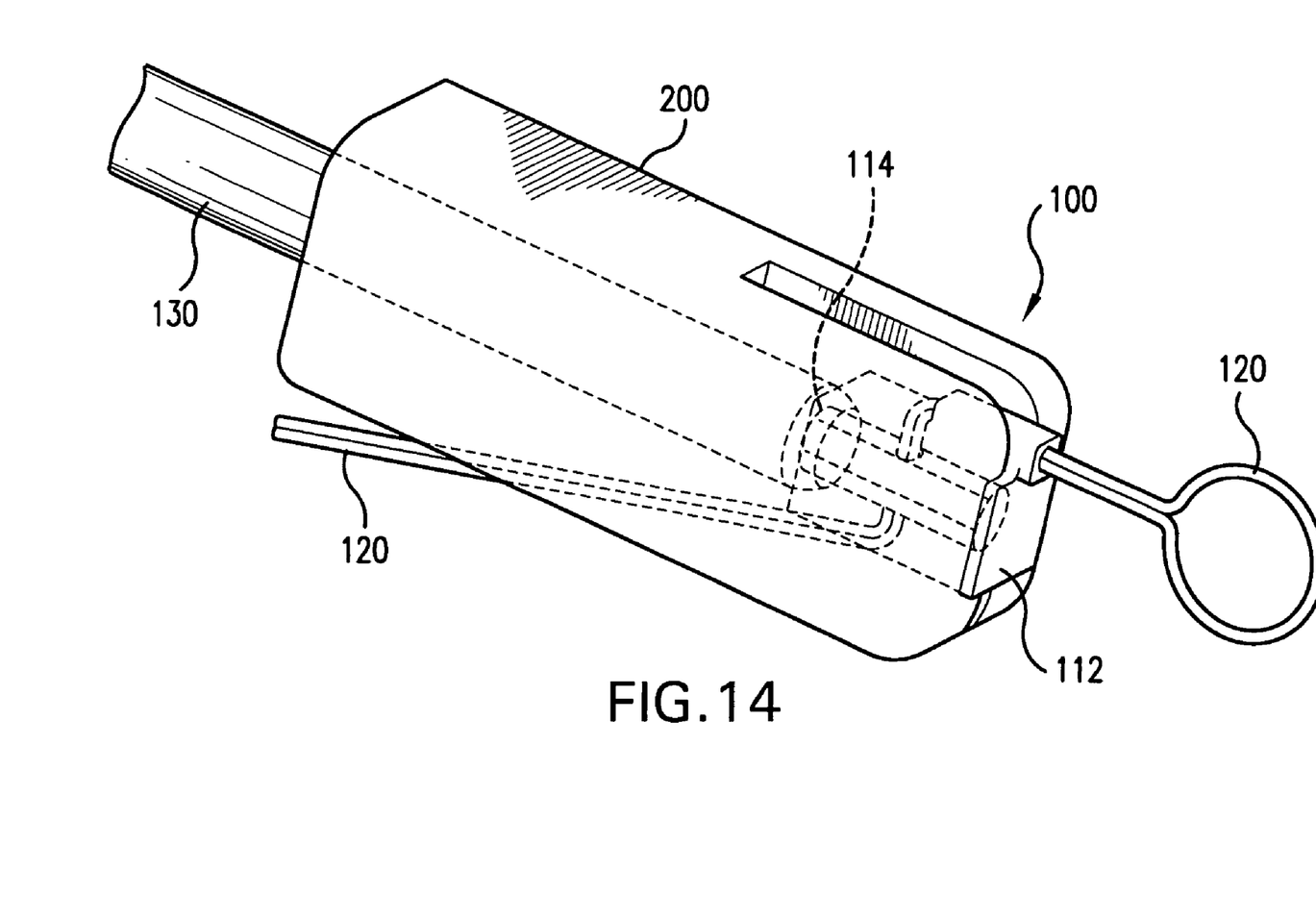
FIG. 14 is a perspective view of the distal end of the system of FIGS. 12 and 13.

FIGS. 12 to 14 show an exemplary embodiment of the invention in which clamping system 100 includes a block of elastic material 112 into which a rotatable element 114 is received. A suture loop 120 passes through block 112 and rotatable element 114. (Rotatable element 14 has a hole 115 passing therethrough and block 112 has a hole 113 passing therethrough). Rotatable element has a top end 116 which may protrude out of block 112 as shown for engagement with a device to rotate element 114. In addition, system 100 may also include a loop holder extension 117 for positioning suture loop 120.

As shown in FIGS. 13 and 14, system 100 may be received into the distal end of an elongated member 200. Elongated member 200 has a lumen or chamber passing therethrough in which rod 130 is received. Preferably, the distal end of rod 130 mates with end 116 of rotatable element 114 such that, rotation of rod 130 rotates rotatable element 114, thereby tightening suture passing through block 112 and rotatable element 114. Specifically, such rotation will wrap the suture around rotatable element 114 in the same way that sutures 20 and 22 were wrapped around rotatable element 14 in clamping system 10, previously described.

As can be seen in FIG. 14, the distal end of elongated member 200 is dimensioned to receive system 100 therein. Optionally, rod 130 may be advanced distally such that system 100 can easily be pushed out of the distal end of elongated member 200. This feature is particularly advantageous when the suture pair or loop passing through system 100 has been clamped into position (i.e.: wrapped around rotatable element 114).

In preferred aspects, the present method uses suture loop 120 to snare the pair of sutures which are to be clamped together. Specifically, loop 120 (or a loop formed by sutures 20 and 22) is wrapped around the suture pair to be clamped. Thereafter, loop 120 is pulled back through system 100 such that the pair of sutures which are to be clamped together are also pulled through system 100 (i.e.: passing through body 112 and rotatable element 114). Then, rod 130 is rotated such that the suture pair is wrapped around rotatable element 114. Finally, rod 130 is advanced distally, pushing system 100 away from the distal end of elongated member 200.

The invention claimed is:

1. A suture clamping system, comprising:
a block of material having a first hole defined therethrough, a second hole formed in and extending part way through the block of material, and a loop holder extension adapted to receive at least one length of suture, the loop holder extension being generally parallel to the second hole and generally perpendicular to the first hole;
a rotatable element received into the second hole formed in the block of material, the rotatable element having a third hole defined therethrough, the rotatable element being rotatable relative to the block to position the first hole defined through the block of material and the third hole defined through the rotatable element in alignment to receive the at least one length of suture, the rotatable element being rotatable to wrap the at least one length of suture around the rotatable element; and
a snare disposed through the first hole and the third hole, and received within the loop holder extension of the block of material, the snare being movable through the first hole, the third hole, and the loop holder extension following capture of the at least one length of suture to position the at least one suture through the first hole and the third hole.

2. The system of claim 1, wherein the rotatable element is rotatable about an axis perpendicular to the direction in which the first hole passes through the block of material and the third hole in the rotatable element.

3. The system of claim 1, wherein the rotatable element is friction-fit into the block of material.

4. The system of claim 1, wherein the block of material is made of silicone.

5. The system of claim 1, wherein the block of material is made of polypropylene.

6. The system of claim 1, wherein the rotatable element is made of a material chosen from the group consisting of stainless steel and moldable plastic.

7. The system of claim 1, wherein an end of the rotatable element projects out of the block of material, wherein the end projecting out of the block of material includes a plurality of recesses therein.

8. The system of claim 7, further comprising: a rod operatively associated with the rotatable element, the rod having a plurality of distal projections, wherein a projection is received into each of the recesses on the end of the rotatable element.

9. The system of claim 1, further comprising: a rod having a distal end being operatively associated with an end of the rotatable element to turn the rotatable element.

10. The system of claim 7, further comprising: an elongated positioning member dimensioned to receive both the rod and the block of material therein.

11. The system of claim 10, wherein the block of material is received into a distal end of the elongated positioning member, and wherein the rod is disposed within a chamber passing through the elongated positioning member.

12. The system of claim 11, wherein moving the rod distally pushes the block of material out of the distal end of the positioning member.

* * * * *

UNITED STATES PATENT AND TRADEMARK OFFICE
CERTIFICATE OF CORRECTION

PATENT NO. : 7,416,556 B2  Page 1 of 1
APPLICATION NO. : 10/162630
DATED : August 26, 2008
INVENTOR(S) : Jasper Jackson

It is certified that error appears in the above-identified patent and that said Letters Patent is hereby corrected as shown below:

Title Page
Item 56, References Cited, U.S. Patent Documents, change "3,513,848   5/1970   Winston" to --3,513,848   12/1967   Winston--
Item 56, References Cited, Foreign Patent Documents, change "WO   WO 95/21573   8/1975" to --WO   WO 95/21573   8/1995--

Column 5
Line 8, change "(Rotatable element 14" to --(Rotatable element 114--

Signed and Sealed this

Second Day of February, 2010

David J. Kappos
*Director of the United States Patent and Trademark Office*